United States Patent
Smith

(10) Patent No.: US 7,491,842 B2
(45) Date of Patent: Feb. 17, 2009

(54) PROCESS FOR PRODUCING CARBONYLATION PRODUCTS

(75) Inventor: Warren John Smith, East Riding (GB)

(73) Assignee: BP Chemicals Limited, Middlesex (GB)

( * ) Notice: Subject to any disclaimer, the term of this patent is extended or adjusted under 35 U.S.C. 154(b) by 82 days.

(21) Appl. No.: 10/590,499

(22) PCT Filed: Feb. 9, 2005

(86) PCT No.: PCT/GB2005/000438

§ 371 (c)(1),
(2), (4) Date: Aug. 24, 2006

(87) PCT Pub. No.: WO2005/085162

PCT Pub. Date: Sep. 15, 2005

(65) Prior Publication Data

US 2007/0287853 A1    Dec. 13, 2007

(30) Foreign Application Priority Data

Mar. 3, 2004 (GB) .................................. 0404793.2

(51) Int. Cl.
*C07C 67/36* (2006.01)
*C07C 51/12* (2006.01)

(52) U.S. Cl. ..................................... 560/232; 562/519

(58) Field of Classification Search .................. None
See application file for complete search history.

(56) References Cited

U.S. PATENT DOCUMENTS 5,218,140 A * 6/1993 Wegman ..................... 560/232
6,521,783 B1 * 2/2003 Wegman et al. ............. 560/232

FOREIGN PATENT DOCUMENTS

| EP | 0 353 722 A2 | 2/1990 |
| WO | WO 98/57918 A1 | 12/1998 |
| WO | WO 01/07393 A1 | 2/2001 |
| WO | WO 03/014054 A1 | 2/2003 |

* cited by examiner

*Primary Examiner*—Paul A Zucker
(74) *Attorney, Agent, or Firm*—Nixon & Vanderhye

(57) ABSTRACT

A carbonylation process for producing a carbonylation product by contacting carbon monoxide with a feed comprising an alcohol and/or a reactive derivative thereof in the vapour phase using an heterogeneous heteropolyacid catalyst comprising one or more metal cations selected from Cu, Fe, Ru, Os, Co, Rh, Ir, Ni, Pd and Pt and wherein there is at least 0.5 wt % water present in the feed.

36 Claims, No Drawings

PROCESS FOR PRODUCING CARBONYLATION PRODUCTS

This application is the U.S. National Phase of International Application PCT/GB2005/000438, filed 9 Feb. 2005, which designated the U.S. PCT/GB2005/000438 claims priority to British Application No. 0404793.2, filed 3 Mar. 2004. The entire content of these applications are incorporated herein by reference.

The present invention relates in general to the production of a carbonylation product by the carbonylation of an alcohol and/or a reactive derivative thereof and, in particular, to the production of a carbonylation product by the vapour phase carbonylation of an alcohol and/or a reactive derivative thereof in the presence of water and a heterogeneous carbonylation catalyst.

Acetic acid may be produced by the rhodium-catalysed, iodide-promoted carbonylation of methanol in a homogeneous liquid-phase reaction medium, such as described, for example in U.S. Pat. No. 3,769,329. The rhodium-catalysed, iodide-promoted liquid phase carbonylation of methanol is a well-known process and is operated on a commercial scale. The desirability of employing heterogeneous carbonylation catalysts for the purpose of facilitating product separation from the catalyst has also been recognised. Heterogeneous carbonylation catalysts and their use are described in a number of patent publications including, for example WO 98/57918, EP 0885870 A1 and EP 0353722 A2.

WO 98/57918 describes a process for the production of a carboxylic acid by the carbonylation of an alcohol and/or a reactive derivative thereof in the liquid phase over a heterogeneous carbonylation catalyst comprising a group VIII noble metal species on a polymeric resin having functional groups selected from nitrogen containing heterocycles. Hydrogen is added to the carbonylation to reduce leaching of the active catalytic species from the support material during carbonylation.

EP 0885870 A1 describes a process for the production of carboxylic acid and/or carboxylic acid anhydrides which comprises contacting an alcohol and/or a carboxylic acid ester, optionally water, a first hydrocarbyl halide and/or a hydrocarbyl ether reactant and a second hydrocarbyl halide promoter, with carbon monoxide in the presence of a catalyst comprising an insoluble imidazole-containing resin supporting a Group VIII metal species. The process may be performed in the liquid or the vapour phase.

EP 0353722 A2 describes a process for the vapour phase carbonylation of one or more alcohols, ethers or ether alcohols to esters and, optionally, to carboxylic acids over a solid catalyst comprising a polyoxometalate anion in which the metal is at least one taken from Group V and VI of the periodic table, such as Mo, W, V, Nb, Cr and Ta, complexed with at least one Group VIIIA cation, such as Fe, Ru, Os, Co, Rh, Ir, Ni, Pd and Pt.

U.S. Pat. No. 6,127,432 describes processes for the conversion of a feedstock comprising carbon monoxide and hydrogen to a product stream comprising at least one of an ester, acid, acid anhydride and mixtures thereof. U.S. Pat. No. 6,127,432 also describes a process for converting an alcohol, ether and/or ether alcohol to oxygentated products such as esters, acids, acid anhydrides and mixtures thereof, which process may be conducted in the vapour phase over a heterogeneous alcohol carbonylation catalyst selected from a solid superacid, clay, zeolite or molecular sieve. The alcohol carbonylation catalysts include heteropolyacids comprising a polyoxometalate anion in which a metal, or mixture of metals, selected from Groups 4, 5, 6 and 7 metals is complexed with a cation from a member of Group 7, 8, 9 10 and/or 11 metals, such as Fe, Ru, Os, Co, Rh, Ir, Ni, Pd and Pt. A preferred heteropolyacid comprises $MW_{12}PO_{40}$, wherein M is Ir, Ru, Rh, Pd and combinations thereof. U.S. Pat. No. 6,127,432 states that the stability of the heterogeneous alcohol carbonylation catalyst is improved by use of hydrogen or a feedstock containing hydrogen in the carbonylation process.

We have now found that addition of water to the feed in a vapour phase, heterogeneous carbonylation process utilising an heteropolyacid catalyst comprising one or more metal cations gives improved catalyst activity.

Accordingly, the present invention provides a carbonylation process for the production of a carbonylation product by contacting carbon monoxide with a feed comprising an alcohol and/or a reactive derivative thereof in the vapour phase using an heterogeneous heteropolyacid catalyst comprising one or more metal cations selected from Cu, Fe, Ru, Os, Co, Rh, Ir, Ni, Pd and Pt, characterised in that there is also present in the feed at least 0.5 wt % water.

The present invention also provides for the use of water at a concentration of at least 0.5 wt % in the feed to a carbonylation process to increase the activity of an heterogeneous heteropolyacid catalyst comprising one or more metal cations selected from Cu, Fe, Ru, Os, Co, Rh, Ir, Ni, Pd and Pt in the production of a carbonylation product by contacting carbon monoxide with an alcohol and/or reactive derivative thereof in the vapour phase over said catalyst.

The water may be fresh water and/or recycled water.

Preferably, the water (fresh and/or recycle) in the feed to the carbonylation process is present at a concentration of at least 1 wt %, such as at least 2 wt %. More preferably, the water in the feed to the carbonylation process is present at a concentration of at least 5 wt %.

Preferably, the water (fresh and/or recycle) in the feed to the carbonylation process is present at a concentration of up to 20 wt % water, such as up to 15 wt % water. Most preferably, the water in the feed to the carbonylation process is present at a concentration of 5 to 15 wt %.

By "heteropolyacid catalyst comprising one or more metal cations selected from Cu, Fe, Ru, Os, Co, Rh, Ir, Ni, Pd and Pt", as used herein, is meant an heteropolyacid in which one or more of the hydrogen ions of the free heteropolyacid has been substituted by at least one of the described cations (hereinafter a substituted heteropolyacid). In addition to the one or more metal cations selected from Cu, Fe, Ru, Os, Co, Rh, Ir, Ni, Pd and Pt, the heteropolyacid may comprise further cations, such as "residual" hydrogen ions and/or alkali metal cations selected from Li, Na, Rb and Cs.

Typically, the heteropolyacid anion comprises 2-18 oxygen-linked polyvalent metal atoms, which are known in the art as peripheral atoms. These peripheral atoms surround one or more central atoms in a symmetrical manner. The peripheral atoms are usually one or more of molybdenum, tungsten, vanadium, niobium, chromium and tantalum, but may be or may include other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field such as, for example, the structures known as Keggin, Wells-Dawson and Anderson-Evans-Perloff structures.

The preferred heteropolyacids for use in the process according to the present invention comprise one or more of molybdenum, tungsten, vanadium, niobium, chromium and tantalum as the peripheral atoms and silicon or phosphorus as the central atoms.

Typically the substituted heteropolyacid will comprise 1 to 6% by weight of the substituent metal cation, preferably 3 to 5% by weight. The substituted heteropolyacids usually have a high molecular weight, for example, in the range from 2000 to 8000, preferably in the range 2000 to 4000, and can include dimeric complexes.

Preferably, the substituted heteropolyacid is selected from substituted silicotungstic acids, silicomolybdic acids, phosphotungstic acids, phosphomolybdic acids, such as substituted heteropolyacids of the following free acids:
12-tungstophosphoric acid $H_3[PW_{12}O_{40}] \cdot xH_2O$
12-molybdophosphoric acid $H_3[PMo_{12}O_{40}] \cdot xH_2O$
12-tungstosilicic acid $H_4[SiW_{12}O_{40}] \cdot xH_2O$
12-molybdosilicic acid $H_4[SiMo_{12}O_{40}] \cdot xH_2O$ Preferably, the metal cation is selected from one or more of rhodium, iridium and copper, and in particular is rhodium or iridium. Rhodium is the most preferred metal cation.

The substituted heteropolyacid is preferably supported. Suitably, the support may be selected from oxide supports such as silica, silica/aluminas, zeolites, clays, diatomaceous earths, titania and alumina. Other non-oxide supports that can be used include silicon carbide, organic polymers such as crosslinked polystyrenes and carbons. The support, such as a siliceous support, is suitably in the form of granules, beads, globules, extrudates or pellets.

Where the substituted heteropolyacid is supported the substituted heteropolyacid is typically present at a loading of 20-70% by weight of the total weight of the supported substituted heteropolyacid, that is, the substituted heteropolyacid forms 20-70% by weight of the total weight of the substituted heteropolyacid and the support. Preferably, where the substituted heteropolyacid is supported, the substituted heteropolyacid is present at a loading of 30-65% by weight of the total weight of the supported substituted heteropolyacid.

Preferably, the alcohol is an aliphatic alcohol having 1 to 12 carbon atoms, preferably 1 to 6 carbon atoms, including methanol, ethanol, propanol, isopropanol, the butanols, pentanols and hexanols. A preferred alcohol is methanol.

Reactive derivatives of the alcohol which may be used as an alternative to, or in addition to, the alcohol include one or more dialkyl ethers, esters of the alcohol and alkyl halides. Suitable reactive derivatives of methanol, for example, include methyl acetate, dimethyl ether and methyl iodide. A mixture of an alcohol and a reactive derivative thereof, for example a mixture of methanol and methyl acetate, may also be employed.

Where a reactive derivative such as an ether or an ester of an alcohol is employed together with an alcohol, the ether and/or ester is present in an amount up to equimolar to the amount of water present in the feed.

The reactive derivative such as an ether or an ester of an alcohol may be employed as a fresh feed and/or obtained from a recycle stream.

The carbonylation product is a carboxylic acid and/or the corresponding carboxylic ester. Thus, where methanol is employed as the alcohol feed, the carbonylation product comprises acetic acid and/or methyl acetate.

Water may be produced during the carbonylation process as a by-product of esterification. This water may be recycled to the reactor. It may be necessary to add "fresh" water to the carbonylation reaction feed in addition to any water that may be recycled in order to maintain the desired concentration of water in the feed to the reactor.

The carbon monoxide reactant may be essentially pure or may contain impurities such as carbon dioxide, methane, nitrogen, noble gases and $C_1$ to $C_4$ paraffinic hydrocarbons.

The carbon monoxide (CO) may be present in the reaction at any suitable partial pressure, such as a partial pressure of at least 0.1 bar. More particularly, the CO may be fed to the reactor in a suitable molar ratio to the alcohol feed (and/or reactive derivative), preferably at a CO to alcohol molar ratio of at least 1:1, such as at least 5:1, and/or up to 20:1, most preferably in the range 5:1 to 15:1.

In a preferred embodiment of the present invention, the carbonylation reaction may be performed in the presence of hydrogen. The hydrogen reactant may be fed to the reactor as an essentially pure hydrogen feed or the hydrogen feed stream may contain impurities, such as carbon oxides and nitrogen. Where hydrogen is used in the process of the present invention, it is especially desirable to use synthesis gas as a source of both the hydrogen and the carbon monoxide.

The hydrogen, when present, may be present in the reaction at any suitable hydrogen concentration, such as at a partial pressure of at least 0.1 bar, and is especially fed, either separately from or combined with carbon monoxide, such that the hydrogen to carbon monoxide molar ratio in the reactor is at least 1:20, such as 1:20 to 20:1, most preferably in the range 1:10 to 10:1.

The process of the invention may be operated at below atmospheric pressure, but is preferably operated at a total pressure in the range from 1 to 100 barg, preferably from 1 to 20 barg.

The process is suitably performed at a temperature in the range from 100 to 300° C., the practical upper operating temperature being dependant on the thermal stability of the catalyst. Preferably the temperature is in the range 150 to 250° C., most preferably in the range 200 to 250° C.

The process is suitably performed by contacting the reactants with the catalyst at a gas hourly space velocity (GHSV) in the range from 100 to 10000 $h^{-1}$, Preferably the GHSV is in the range 500 to 5000 $h^{-1}$.

The process may be operated as a batch or continuous process, preferably as a continuous process.

The invention will now be illustrated by reference to the following examples.

EXAMPLES

Catalyst A Preparation

A rhodium-substituted heteropolyacid catalyst was prepared as follows. $RhCl_3 \cdot H_2O$ (Aldrich, FW=209.26, 0.774 g) was dissolved in methanol (ca 200 ml) with stirring for 30 minutes. After stirring of the rhodium mixture, 12-tungstophosphoric acid (H3[PW12O40].xH20, Aldrich, FW 2280 g/mol, 10.657 g) was added with stirring for 1 hour. 6.416 g of silica (Grace, grade G57, FW=60 g/mol, 1-2 mm particle size) was then added. The solution was then stirred for 4 hours. After 4 hours the flask was transferred to a rotary evaporator and the methanol removed under reduced pressure of 337 mbar for 1 hour to yield a red/orange solid. This solid was crushed using a mortar and pestle and then sieved to give a catalyst of particle size 0.5-1.0 mm.

Catalyst Testing Procedure

A number of experiments were carried out at varying water concentrations in the feed and at two different gas hourly space velocities (GHSV).

Examples 1 to 3

5 ml (approx. 5 g) of catalyst A was charged to a quartz tube reactor with a supportive frit positioned in the middle of the tube. The reactor was then further filled with borosilicate glass beads above the catalyst. The reactor was positioned in the middle of a vertical furnace with insulating lagging at the top and bottom of the furnace. Carbon monoxide and methanol were fed to the quartz reactor in a molar ratio of CO:MeOH of 9:1. Carbon monoxide at a gas flow rate of 150 ml/min was fed into the top of the reactor via a flow meter. Once stable flow was achieved after 2-3 minutes, the furnace was heated gradually (5° C./min) to 100° C. The furnace remained at 100° C. for 20 min to remove the majority of the water from the catalyst after which time the furnace was heated gradually (5° C./min) to 230° C. The system was left at temperature for 15 min to fully equilibrate and then liquid methanol and water (where used) (see Table 1 below for liquid feed flow parameters) were fed to the top of the reactor via a syringe pump. The liquid and gaseous reactants passed down through the reactor and into a liquid trap. The liquid trap comprised a coil condenser immersed in an ice-bath, where the liquid products were isolated. The gaseous products were vented via a T-piece containing a septum for taking gas samples via a gas syringe. Typically, the liquid trap was changed every hour and a gas sample was taken during the middle of each time segment. Liquid samples were analysed on a gas chromatograph equipped with a boiling point column and a TCD detector. Gas samples were analysed on a four-column gas chromatograph. Post-reaction the system was completely purged with nitrogen before removing the reactor from the rig. The GHSV was 1800/h. Acetic acid and methyl acetate were products of the reaction.

The results of Examples 1 to 3 are given in Table 2 below.

Experiment A

The catalyst testing procedure was repeated as for Examples 1 to 3 except that no water was added to the carbonylation reaction feed. The results of Experiment A are given in Table 2 below.

Examples 4 to 5

The catalyst testing procedure was repeated as for Examples 1 to 3 except that a GHSV of 900/h and 10 ml of catalyst A was used. The results of Examples 4 to 6 are given in Table 3 below.

Experiment B

The catalyst testing procedure was repeated as for Examples 4 to 5 except that no water was added to the carbonylation reaction feed. The results of Experiment B are given in Table 3 below.

TABLE 1

| Liquid feed parameters | | |
| --- | --- | --- |
| Water in Feed (wt %) | MeOH Feed Rate (ml/h) | $H_2O$ Feed Rate (ml/h) |
| 0 | 1.60 | 0.00 |
| 5 | 1.52 | 0.08 |
| 10 | 1.44 | 0.16 |
| 15 | 1.36 | 0.24 |

TABLE 2

Results for Examples 1 to 3 and Experiment A
Conditions: 230° C., 1 barg, reaction time of 3 hours.

| Example/Experiment | Water Level (wt %) | MeOH conv. (%) | Product selectivity (%) |
| --- | --- | --- | --- |
| A | 0 | 17.8 | 94.0 |
| 1 | 5 | 22.7 | 95.8 |
| 2 | 10 | 32.8 | 95.9 |
| 3 | 15 | 29.3 | 95.5 |

TABLE 3

Results for Examples 4 to 5 and Experiment B
Conditions: 230° C., 1 barg, reaction time of 3 hours.

| Example/Experiment | Water Level (wt %) | MeOH conv. (%) | Product selectivity (%) |
| --- | --- | --- | --- |
| B | 0 | 22.0 | 98.1 |
| 4 | 5 | 23.0 | 98.9 |
| 5 | 10 | 23.8 | 98.9 |

The results shown in Tables 2 and 3 demonstrate that by increasing the amount of water in the feed to the carbonylation reaction improved methanol conversion may be achieved. An increase in product selectivity is also observed in the presence of water co-feed compared to its absence. The increases in activity and selectivity are also more pronounced in the Experiments at higher space velocities in the reactor. Thus, in Example 2, for example, shows that the methanol conversion is increased from 17.8wt % with no water co-feed to 32.8 wt % at a 10 wt % water co-feed, whilst the corresponding product selectivity increases from 94.0% to 95.9%.

The invention claimed is:

1. A carbonylation process for the production of a carbonylation product, comprising contacting carbon monoxide with a feed comprising an alcohol and/or a reactive derivative thereof in the vapour phase using an heterogeneous heteropolyacid catalyst comprising one or more metal cations selected from Cu, Fe, Ru, Os, Go, Rh, ir, Ni, Pd and Pt, wherein there is also present in the feed at least 0.5 wt % water, and wherein the water in the feed is selected from fresh and recycle water.

2. Process according to claim 1 wherein the feed comprises at least 1 wt % water.

3. A process according to claim 1 wherein the feed comprises up to 20 wt % water.

4. A process according to claim 1 wherein the feed comprises 5 to 15 wt % water.

5. A process according to claim 1 wherein the heteropolyacid comprises 1 to 6 wt % metal cation(s).

6. A process according to claim 1 wherein the heteropolyacid catalyst comprises a metal cation selected from rhodium, iridium and copper.

7. A process according to claim 6 wherein the metal cation is rhodium.

8. A process according to claim 1 wherein the heteropolyacid comprises a peripheral atom selected from the group consisting of molybdenum, tungsten, vanadium, niobium, chromium and tantalum and a central atom selected from silicon and phosphorus.

9. A process according to claim 1 wherein the heteropolyacid is selected from the group consisting of substituted silicotungstic acids, silicomolybdic acids, phosphotungtic acids and phosphomolybdic acids.

10. A process according to claim 1 wherein the heteropolyacid comprises one or more further cations selected from residual hydrogen ions and alkali metal cations.

11. A process according to claim 1 wherein the heteropolyacid catalyst is supported on a support.

12. A process according to claim 11 wherein the support is selected from an oxide support and a non-oxide support.

13. A process according to claim 12 wherein the oxide support is selected from the group consisting of silica, alumina, silica-aluminas, zeolites, clays, diatomaceous earths and titania.

14. A process according to claim 12 wherein the non-oxide support is selected from the group consisting of silicon carbide, carbons and organic polymers.

15. A process according to claim 11 wherein the heteropolyacid comprises 20 to 70% by weight based on the total weight of heteropolyacid and support.

16. A process according to claim 1 wherein the alcohol is a $C_1$ to $C_{12}$ aliphatic alcohol.

17. A process according to claim 16 wherein the alcohol is selected from methanol, ethanol, propanol, isopropanol, the butanols, the pentanols and the hexanols.

18. A process according to claim 1 wherein the reactive derivative of the alcohols is selected from at least one of a dialkyl ether, an ester of the alcohol and an alkyl halide.

19. A process according to claim 18 wherein the reactive derivative is selected from at least one of methyl acetate, dimethyl ether and methyl iodide.

20. A process according to claim 1 wherein the feed comprises an alcohol and a reactive derivative thereof.

21. A process according to claim 20 wherein the reactive derivative is an ether or an ester of the alcohol.

22. A process according to claim 21 wherein the ether and/or the ester is present in an amount up to equimolar to the amount of water in the feed.

23. A process according to claim 1 wherein the carbonylation product is selected from at least one of a carboxylic and a carboxylic acid ester.

24. A process according to claim 23 wherein the carbonylation product is selected from at least one of acetic acid and methyl acetate.

25. A process according to claim 1 wherein the carbon monoxide to alcohol molar ratio is in the range 5:1 to 15:1.

26. A process according to claim 1 wherein the feed also comprises hydrogen.

27. A process according to claim 26 wherein the hydrogen to carbon monoxide molar ratio is in the range 1:20 to 20:1.

28. A process according to claim 1 wherein the carbon monoxlde is used in the form of synthesis gas.

29. A process according to claim 1 wherein the process is carried out at a temperature in the range 100 to 300° C.

30. A process according to claim 1 wherein the process is carried out at a pressure in the range 1 to 100 barg.

31. A process according to claim 1 wherein the gas hourly space velocity is in the range of 100 to 10000 $h^{-1}$.

32. A process according to claim 1 wherein the process is carried out as a continuous process.

33. A process according to claim 1 wherein the feed comprises at least 2 wt % water.

34. A process according to claim 1 wherein the feed comprises at least 5 wt % water.

35. A process according to claim 1 wherein the feed comprises up to 15 wt % water.

36. A carbonylation process for the production of a carbonylation product by contacting carbon monoxide with a feed comprising methanol in the vapour phase using a heterogeneous heteropolyacid catalyst comprising one or more metal cations selected from rhodium, iridium and copper, wherein there is also present in the feed 5 to 15 wt % water, and wherein the water in the feed is selected from fresh and recycle water.

* * * * *